United States Patent [19]

Chen et al.

[11] Patent Number: 5,210,347

[45] Date of Patent: May 11, 1993

[54] PROCESS FOR THE PRODUCTION OF HIGH CETANE VALUE CLEAN FUELS

[75] Inventors: Catherine S. H. Chen, Berkeley Heights; Dennis H. Hoskin, Westampton; Suzanne E. Schramm, Robinsville, all of N.J.

[73] Assignee: Mobil Oil Corporation, Fairfax, Va.

[21] Appl. No.: 764,258

[22] Filed: Sep. 23, 1991

[51] Int. Cl.$^5$ ............................ C10L 1/16; C07C 2/02
[52] U.S. Cl. ........................................ 585/14; 585/12; 585/255; 585/517; 585/521; 585/524; 585/530; 585/533
[58] Field of Search .................... 585/14, 12, 255, 517, 585/521, 524, 530, 533

[56] References Cited

U.S. PATENT DOCUMENTS

| | | | |
|---|---|---|---|
| 4,317,948 | 3/1982 | Heckelsberg | 585/329 |
| 4,568,786 | 2/1986 | Chen et al. | 585/517 |
| 4,658,079 | 4/1987 | Chen | 585/517 |
| 4,827,064 | 5/1989 | Wu | 585/10 |
| 4,855,527 | 8/1989 | Page et al. | 585/527 |
| 4,962,249 | 10/1990 | Chen et al. | 585/533 |
| 5,113,030 | 5/1992 | Chen et al. | 585/12 |

*Primary Examiner*—Anthony McFarlane
*Assistant Examiner*—Nhat D. Phan
*Attorney, Agent, or Firm*—Alexander J. McKillop; Malcolm D. Keen; L. G. Wise

[57] ABSTRACT

The 350°-650° F. (177°-343° C.) portion of the product from the oligomerization of light olefin with surface deactivated shape selective medium pore zeolite catalyst particles comprises olefinic hydrocarbons having unique and desirable structures as precursors for high cetane value clean fuels. These oligomers are near linear in structure and contain no aromatics. Following hydrogenation they produce cetane values between 50 and 75. When the near linear olefinic hydrocarbons from surface deactivated zeolite catalyzed oligomerization of light olefins are subjected to ethene metathesis to alpha olefins and oligomerization following the process of Chen et al in U.S. Pat. No. 4,962,249 the overall process reaction product comprises a mixture of a 650° F.+ portion comprising high VI lubricant and a 350°-650° F. portion comprising high cetane clean fuels precursor. Hydrogenation of the 350°-650° F. portion provides an aromatics-free fuel with a cetane value between 50-75 containing less than 0.5 wt % naphthenes. The combined process results in the co-production of high cetane clean fuels and high VI synthetic lubricant.

20 Claims, No Drawings

PROCESS FOR THE PRODUCTION OF HIGH CETANE VALUE CLEAN FUELS

RELATED ART

This application is related to U.S. Pat. No. 4,962,249 to C. S. H. Chen and M. S. Wu, incorporated herein by reference in its entirety.

This invention relates to a process for the co-production of hydrocarbon lubricants and high cetane value hydrocarbon fuels from near linear alpha olefins derived from inexpensive lower alkenes by employing the intermediate production of near linear internal olefin oligomers. More particularly, the invention relates to the discovery that a complex mixture of higher alpha olefins produced by metathesis of slightly branched internal higher olefins can be oligomerized to provide superior lubricants and high cetane value fuels. The invention also includes the discovery that high cetane value fuel is produced free of aromatics from the oligomerization of lower olefins to slightly branched olefinic higher hydrocarbons.

BACKGROUND OF THE INVENTION

In the processes known in the art for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2$-$C_8$ alkenes may be converted. A typical reactive feedstock consists essentially of $C_3$-$C_6$ mono-olefins, with varying amounts of nonreactive paraffins and the like being acceptable components.

U.S. Pat. Nos. 4,520,221, 4,568,786 and 4,658,079 to C. S. H. Chen et al., incorporated herein by reference in their entirety, disclose further advances in zeolite catalyzed olefin oligomerization. These patents disclose processes for the oligomerization of light, or lower, olefins using zeolite catalyst such as ZSM-5. The oligomers so produced are near linear in structure and contain internal olefin unsaturation. These unique olefinic oligomers are produced by surface deactivation of the ZSM-5 type catalyst by pretreatment with a surface-neutralizing base. The processes of Chen et al. provide a particularly useful means to prepare slightly branched higher olefinic hydrocarbons from inexpensive lower olefins, particularly propylene.

In U.S. Pat. No. 4,962,249, near linear higher olefinic hydrocarbons produced by the oligomerization of lower olefins using surface deactivated zeolite catalyst are converted to a mixture comprising slightly branched and linear higher alpha olefins. These alpha olefins are oligomerized to lubricant grade hydrocarbons in contact with cationic, Ziegler or coordination catalyst. Oligomerization of the aforementioned alpha olefins using reduced valence state Group VIB metal oxide catalyst on porous support provides a hydrocarbon lubricant with a viscosity index of greater than 130 at 100° C. Olefin metathesis with ethene, as described in *Olefin Metathesis* by K. J. Ivin, published by Academic Press, Chapter 5, is applied to the internal olefinic oligomers of Chen et al. to provide a route to the alpha olefins suitable for the production of synthetic lubricants, utilizing the process described in U.S. Pat. Nos. 4,827,064 and 4,827,073 to M. Wu, incorporated herein by reference. The lubricants recovered comprise the 650° F.+ (343° C.+) fraction of the oligomerization reaction product.

It is an object of the present invention to provide a process for the co-production of high VI synthetic lubricants and high cetane value fuel from slightly branched higher internal olefins.

It is another object of the present invention to provide a process for the production of high cetane value fuel from slightly branched hydrocarbon oligomers.

A further object of the present invention is to provide a process for the oligomerization of inexpensive light olefins to slightly branched olefins for the direct co-production of synthetic lubricants and high cetane fuel.

SUMMARY OF THE INVENTION

It has been discovered that the 350°-650° F. (177°-343° C.) portion of the product from the oligomerization of light olefin with surface deactivated shape selective medium pore zeolite catalyst particles comprises olefinic hydrocarbons having unique and desirable structures as precursors for high cetane value clean fuels where, in this invention, the term clean fuels relates particularly to the absence of aromatics in the fuel. These oligomers are near linear in structure and contain no aromatics. As a result, following hydrogenation they produce cetane values between 50 and 75. When the near linear olefinic hydrocarbons from surface deactivated zeolite catalyzed oligomerization of light olefins are subjected to ethene metathesis to alpha olefins and oligomerization following the process of Chen et al in U.S. Pat. No. 4,962,249 the overall process reaction product comprises a mixture of a 650° F.+ portion comprising high VI lubricant and a 350°-650° F. portion comprising high cetane clean fuels precursor. Hydrogenation of the 350°-650° F. portion provides an aromatics-free fuel with a cetane value between 50-75. Accordingly, the combined process results in the co-production of high cetane clean fuels and high VI synthetic lubricant.

More particularly, a process for the co-production of lubricant range hydrocarbons and hydrocarbon fuel having high cetane number has been discovered which comprises the following steps:

a) contacting a feedstream comprising lower olefinic hydrocarbons with surface deactivated acidic, medium pore, shape selective metallosilicate catalyst particles under oligomerization conditions whereby a product stream comprising aromatics-free slightly branched internal olefin oligomers is produced;

b) contacting the slightly branched oligomer and excess ethylene feedstream with metathesis catalyst in a reaction zone under metathesis conditions whereby said internal olefin oligomers are converted to reaction product comprising slightly branched alpha-olefin oligomers and unconverted oligomer;

c) contacting the metathesis reaction product with reduced valence state Group VIB metal catalyst on porous support under oligomerization conditions and recovering a reaction product containing a 350° F.-650° F. fuel boiling range portion and a 650° F.+ lubricant range portion having high viscosity index;

d) separating and hydrogenating the fuel boiling range portion whereby a hydrocarbon fuel having cetane number between 50 and 75 is produced.

The invention also comprises a process for the production of hydrocarbon fuels having high cetane value, comprising, contacting a feedstream comprising lower olefinic hydrocarbons with surface deactivated acidic, medium pore, shape selective metallosilicate catalyst particles under oligomerization conditions whereby a product stream comprising aromatics-free near linear olefinic oligomers is produced; hydrogenating at least a portion of the product stream and recovering a 350° F.–650° F. fuel boiling range fraction having a cetane value between 50 and 70.

DETAILED DESCRIPTION OF THE INVENTION

The olefin oligomers used as starting material in the present invention are prepared from $C_3$–$C_5$ olefins according to the methods presented by Chen et al. in the aforementioned patents cited and N. Page and L. Young in U.S. Pat. No. 4,855,527 and incorporated herein by reference. Shape-selective oligomerization, as it applies to conversion of $C_3$–$C_5$ olefins over ZSM-5, is known to produce higher olefins up to $C_{30}$ and higher. Reaction conditions favoring higher molecular weight products are low temperature (200°–260° C.), elevated pressure (about 2000 kPa or greater) and long contact times (less than 1 WHSV). The reaction under these conditions proceeds through the acid catalyzed steps of oligomerization, isomerization-cracking to a mixture of intermediate carbon number olefins, and interpolymerization to give a continuous boiling product containing all carbon numbers. The channel system of ZSM-5 type catalysts impose shape selective constraints on the configuration of large molecules, accounting for the differences with other catalysts.

The shape-selective oligomerization/polymerization catalysts preferred for use herein to prepare the olefin oligomers used as starting material in the invention include the crystalline aluminosilicate zeolites having a silica to alumina molar ratio of at least 12, a constraint index of about 1 to 12 and acid cracking activity of about 50–300. Representative of the ZSM-5 type zeolites are ZSM-5, ZSM-11, ZSM-12, ZSM-23, ZSM-35 and ZSM-38. ZSM-5 is disclosed and claimed in U.S. Pat No. 3,702,886 and U.S. Pat. No. Re. 29,948; ZSM-11 is disclosed and claimed in U.S. Pat. No. 3,709,979. Also, see U.S. Pat. Nos. 3,832,449 for ZSM-12; 4,076,842 for ZSM-23; 4,016,245 for ZSM-35 and 4,046,839 for ZSM-38. The disclosures of these patents are incorporated herein by reference. A suitable shape selective medium pore catalyst for fixed bed is a small crystal H-ZSM-5 zeolite (silica:alumina ratio=70:1) with alumina binder in the form of cylindrical extrudates of about 1–5 mm. Unless otherwise stated in this description, the catalyst shall consist essentially of ZSM-5, which has a crystallite size of about 0.02 to 0.05 micron, or ZSM-23. Other pentasil catalysts which may be used in one or more reactor stages include a variety of medium pore siliceous material disclosed in U.S. Pat. Nos. 4,414,423 and 4,417,088, incorporated herein by reference.

The acid catalysts are deactivated by pretreatment with a surface-neutralizing base, as disclosed by Chen et al. and Page et al. in the aforementioned patents incorporated by reference. Surface deactivation is carried out using bulky or sterically hindered bases, typically those comprising trialkyl substituted pyridines. These hindered bases have very limited access to the internal pore structure of the catalyst, leaving the pores active sites for near linear oligomerization. However, active surface sites which are not constrained, as pores are, to low branching oligomerization are neutralized.

Considering propylene oligomerization for purposes of illustration, the olefinic oligomerization-polymerization products include $C_{10}+$ substantially linear aliphatic hydrocarbons. The ZSM-5 catalytic path for propylene feed provides a long chain with approximately one to two lower alkyl (e.g., methyl) substituents per 12 carbon atoms in the straight chain.

When propylene or butene are oligomerized according to processes described herein, a unique mixture of liquid hydrocarbon products are formed. More particularly, this mixture of hydrocarbons may comprise at least 95% by weight of mono-olefin oligomers of the empirical formula:

$$(C_nH_{2n})_m$$

where n is 3 or 4 and m is an integer from 1 to approximately 10, the mono-olefin oligomers comprising at least 20 percent by weight of olefins having at least 12 carbon atoms. Those olefins having at least 12 carbon atoms have an average of from 0.80 to 2.50 methyl side groups per carbon chain. The olefin side groups are predominantly methyl.

It will be understood that methyl side groups are methyl groups which occupy positions other than the terminal positions of the first and last (i.e., alpha and omega) carbon atoms of the longest carbon chain. This longest carbon chain is also referred to herein as the carbon backbone chain of the olefin. The average number of methyl side groups for the $C_{12}$ olefins may comprise any range within the range of 0.80 to 2.50.

These oligomers may be separated into fractions by conventional distillation separation. When propylene is oligomerized, olefin fractions containing the following number of carbon atoms can be obtained: 6, 9, 12, 15, 18 and 21. When butene is oligomerized, olefin fractions containing the following numbers of carbon atoms may be obtained: 8, 12, 16, 20, 24 and 28. It is also possible to oligomerize a mixture of propylene and butene and to obtain a mixture of oligomers having at least 6 carbon atoms.

Page and Young (allowed application Ser. No. 105,438, filed Oct. 7, 1987) described these new olefins as multi-component mixtures of propylene oligomers having relatively few branching methyl groups on the carbon backbone. As an example of branching, the dodecene fraction prepared from propylene and HZSM-23 [ZSM23-dodecenes] typically has 1.3 methyl branches. This can be reduced to 1.0 or less by varying reaction conditions.

OLEFIN METATHESIS

The metathesis of the slightly branched olefinic hydrocarbons resulting from the olefin oligomerization operation is carried out to provide alpha olefins in a primary reaction which can be thought of as comprising the breaking of two unsaturated bonds between first and second carbon atoms and between third and forth carbon atoms, respectively, and the equilibrium formation of two new alpha olefinic bonds in different molecules as illustrated in the following formulas employing ethylene as the feed alpha-olefin:

1) from trisubstituted olefins

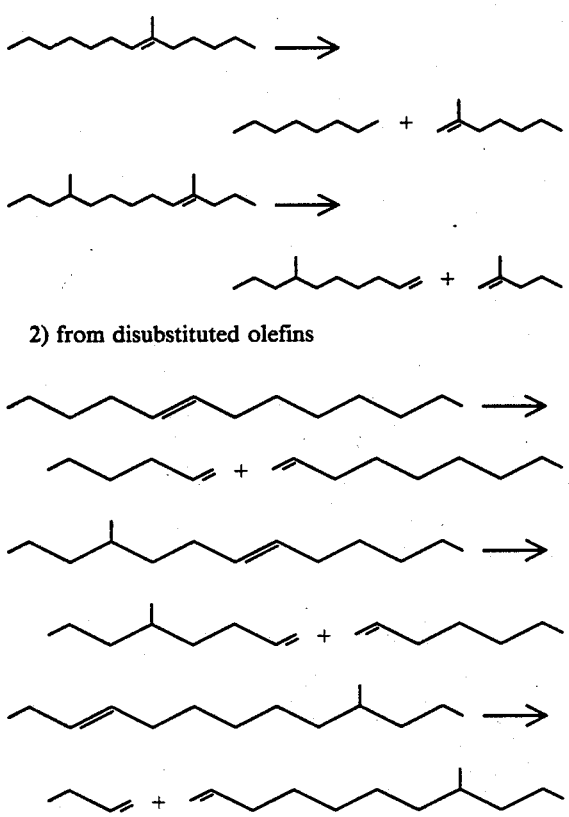

2) from disubstituted olefins

The equilibrium is displaced to the right in the presence of excess ethylene.

The reaction produces linear alpha olefins, branched alpha olefins and vinylidene olefins. The structure and molecular weight of the product olefins depend on the structure of the starting oligomers. For olefins of carbon number $C_n$ which have undergone the metathesis with ethylene, the product olefins have an average molecular weight, on a molar basis, of $C_{n/2}+1$.

Trisubstituted olefins account for a major share of olefins in the slightly branched olefin oligomers. Where these trisubstituted olefins are isoolefinic they account for a major share, as well, of the methyl branching in the olefin oligomer. Their reaction in metathesis with ethylene produces an alpha olefin and a vinylidenic olefin, as already shown. Further, it is known that vinylidene olefins are unreactive in reduced chromium oxide catalyzed and Ziegler catalyst catalyzed oligomerization. Accordingly, the olefin metathesis reaction of slightly branched olefin described here produces a mixture of olefins where only a portion, alpha olefins, are oligomerizable with Ziegler or chromium catalyst to higher lubricant grade hydrocarbon oligomers. A large portion of the methyl branching in the starting olefins is effectively removed from inclusion in higher oligomers produced by coordination catalyst by conversion to vinylidene structures through metathesis with ethylene.

In general any of the $C_{2-8}$ alpha olefins can be reacted with the oligomerization product effluent in the metathesis operation herein. Some specific examples of such alpha-olefins are ethylene, propylene, 1-butene, 1-pentene, 1-hexene, 1-octene, and the like with ethylene being preferred.

Any of the catalysts heretofore employed in olefin metathesis are suitably utilized in the metathesis conversion herein. Many of these catalyst have been reported in the prior art. Preferably, the catalyst is one of molybdenum, tungsten, or rhenium oxide deposited on a support of silica, alumina, silica-alumina or aluminum phosphate. An additional metal oxide, e.g., a rare earth metal oxide, can also be present as is known. Prior to its use, the catalyst is activated by calcination carried out in a conventional manner. A particularly suitable catalyst is molybdenum oxide supported on a mixture of amorphous precipitated silica and colloidal silica. A preferred catalyst is rhenium oxide on alumina. Cocatalysts, including tetraalkyl tin, are useful. A particularly preferred catalyst is rhenium oxide on gamma-alumina plus tetramethyl tin co-catalyst.

Suitable conditions for the metathesis reaction include a pressure of from about 50–35000 KPa, a temperature of from about 0° C. to about 500° C., and space velocities of from about 1 to about 300 WHSV based on the nature of the metathesis catalyst. Although the activity of the catalyst is suitable within the broad ranges mentioned above, increased activity is generally found when the pressure is from about 700 to about 3500 KPa, the temperature range is from about 20°–100° C., and the WHSV is from about 0.5 to about 1000. The process can be carried out either in the presence or absence of a diluent. Diluents comprising paraffinic and cycloparaffinic hydrocarbons can be employed. Suitable diluents are, for example, propane, cyclohexanes, methylcyclohexane, normal pentane, normal hexane, isoctane, dodecane, and the like, or mixtures thereof, including primarily those paraffins and cycloparaffins having up to 12 carbon atoms per molecule. The diluent should be nonreactive under the conditions of the reaction. The reaction can also be carried out in a single unit or a battery of units employing the same or a different catalyst.

The amount of alpha-olefin employed in the metathesis conversion can vary widely and will depend in part on the degree of unsaturation in the higher olefin feed which can be readily quantified employing known techniques, e.g., bromine number. Generally, the alpha-olefin, particularly, will be present in stoichiometric excess of the amount theoretically required but can be substantially less than this. The amount of alpha olefin should be an amount sufficient to suppress the self-metathesis reaction which can occur between two molecules of the near linear olefin feedstock. When ethylene is used as the alpha olefin that amount is typically about a two to five molar excess. If desired, excess alpha-olefin can be separated from the metathesis product effluent and recycled to this stage.

It has been discovered that in the metathesis reaction between the near linear higher olefins and ethylene trisubstituted olefins are less active than disubstituted olefins. The conversion of disubstituted olefins proceeds effectively at ambient temperature (23° C.) in the presence of a cocatalyst $Sn(CH_3)_4$, or at 75°–100° C. in the absence of a cocatalyst $Sn(CH_3)_4$. Trisubstituted olefins, i.e., those containing isoolefin groups, are not converted in the absence of a cocatalyst $Sn(CH_3)_4$ even at elevated temperature (75° C). Optionally, this relationship can be readily utilized to reduce the extent of trisubstituted olefin metathesis to produce vinylidene olefins in favor of predominantly disubstituted olefin metathesis with ethylene to produce alpha olefins.

The primary purpose of performing co-metathesis reactions of near-linear propylene oligomers with ethylene is to produce alpha-olefins. The alpha-olefins so produced are complex mixtures containing two types of structures. One type is linear, but contains both even and odd number carbons, and a mixture of different molecular weights. The other is near-linear with one or two methyl branches, and also contain both even and odd number carbons, and a mixture of different molecular weights. Alpha-olefins are known to be polymerizable by chromium catalysis to produce high VI lubricants.

ALPHA OLEFIN OLIGOMERIZATION

The olefins used to prepare lubes and high cetane value fuels products herein are from the co-metathesis reactions between propylene oligomers and ethylene. The lubes and fuel products were prepared by using activated Cr (3%) on silica catalyst as described in the previously cited U.S. Pat. Nos. to M. Wu. The low branch ratio lubes comprise the 650° F.+ fraction of the oligomerization product recovered preferably by distillation.

The near linear alpha olefins oligomerized in this invention to provide high VI lubricant are characterized as having branching confined predominantly to the pendant alkyl group of the oligomer lubricant molecule. While it is known and taught in the cited Wu patents that branching in the backbone of the lubricant molecule adversely effects VI, high VI lubes can be prepared from slightly branched alpha olefins by reduced chromium catalysis if those branches are restricted predominantly to the pendant alkyl group of the oligomer molecule.

HIGH CETANE VALUE FUEL RECOVERY

The 650° F.+ lubes described above are co-produced with 650° F.− products in 3 steps:
(1) shape selective oligomerization of lower olefins (e.g., propylene) to higher near-linear internal olefins;
(2) co-metathesis reaction of the near-linear olefins with ethylene to 1-olefins; and
(3) polymerization of the resulting alpha olefins by chromium catalysis to high VI lubes and 650° F.− products.

The 350°-650° F. portion of the 650° F.− products have unique and desirable structures as precursors for high cetane clean fuels. They contain both the initial near-linear oligomers unconverted in step 2 and vinylidene olefins formed in step 2 but not polymerized by Cr catalysis in step 3. After hydrogenation, these products exhibit high cetane numbers as determined by a reliable H NMR method and low temperature ignition behavior. Cetane number was also determined on several samples by ASTM method.

The 350°-650° F. fraction of the near-linear internal olefins obtained in step 1 is also a precursor of high cetane clean fuels. The present fuel precursors contain a significant portion of vinylidene olefins as well as near-linear internal olefins. After hydrogenation, the fuels contain paraffins with 1 to 2 methyl side chains per main chain, derived from the near-linear internal olefins. A significant portion will have only one methyl side chain on number 2 carbon atom of the main chain, as derived from the vinylidene olefins. There are no aromatics present in either fuel derived from near linear internal olefins from zeolite catalyzed oligomerization of lower olefins or from reduced chromium catalyzed oligomerization of alpha olefins, as produced from the foregoing steps 1-3. After hydrogenation, the fuels have cetane numbers ranging from 55 to 75, as determined by ASTM method and/or from NMR analysis.

The following Examples illustrate the process of the present invention for the production of high cetane value clean fuels.

EXAMPLE I

Near-linear internal olefins are prepared by oligomerization of propylene in a continuous stirred tank reactor (CSTR) using surface deactivated ZSM-23 as the catalyst at 200° C., 900 psig and 0.3 weight hourly space velocity (WHSV) in a single pass. The conversion of propylene is 91%. The product oligomers contain 21.4% of internal olefins having a carbon number equal to or less than $C_{11}$ and 78.6% of internal olefins having a carbon number equal to or greater than $C_{12}$. The $C_{11}-$ olefins are removed by fractional distillation. For the co-metathesis reaction with ethylene, the $C_{12}+$ olefins are purified by percolating through activated alumina followed by treating with Zeolite 13X and Catalyst R3-11 (Chemical Dynamics Corporation). Activated $Re_2O_7/Al_2O_3$ containing 12% Re and $Sn(CH_3)_4$ at 1:1 mole ratio are used as cocatalysts. The co-metathesis reaction is carried out in a 750 ml Parr reactor equipped with two gas inlets and a sampling dip tube with filter at its tip. A catalyst addition device with a door at its bottom, which could be opened by applying a pressure, is attached to a gas inlet under the reactor cap above the reaction mixture. In a glove box, 75 grams of the purified oligomers is charged into the Parr reactor. The catalyst device is detached from the reactor cap and 6 grams of the activated $Re_2O_7/-Al_2O_3$ are weighed into the device. The $Sn(CH_3)_4$ is syringed into the catalyst device from its solution in the oligomers making certain that the catalyst is evenly wet. The catalyst device is reattached and the Parr reactor is closed. The reactor is then taken out of the glove box and assembled in the laboratory. Two hundred psi ethylene is introduced into the reactor through one gas inlet, and while stirring, the rest of the ethylene (a total of 800 psi) is introduced through the other gas inlet to which the catalyst device is attached. The pressure pushes the door open and the catalyst is carried into the reaction mixture by the incoming ethylene. The reaction mixture is kept at the ambient temperature (25° C.). Liquid samples are withdrawn periodically and analyzed by GC. The reaction takes about 24 hours to reach equilibrium at which time 80% of the oligomers are co-metathesized. The excess ethylene is discharged and the reactor while still closed is carried back to the glove box where the product is discharged and used directly for reduced $Cr/SiO_2$ catalyzed polymerization according to the previously cited process of M. Wu. Fifty grams of the liquid product and 4 grams of activated $Cr/SiO_2$ (3% Cr) are charged into a 450 ml Parr reactor. The reactor is closed, taken out of the glove box and assembled in the laboratory for polymerization. The temperature is raised to 110° C. and kept there for 24 hours. The reactor is cooled down and opened. The catalyst is filtered off by suction and the water-white product is hydrogenated over Pd/C at 50° C. and distilled in vacuum to obtain the following products: 650+° F. lube:

Yield: 54.1%, Viscosity at 100° C.: 50 cS; VI: 164; 480°-650° F. diesel fuel:

Yield:20.5%, NMR estimated cetane number 68; no aromatics

Ignition behavior: T5=245.9° C.; T10=236.8° C.

T20=229.8° C.
350°-480° F. kerosene/jet fuel:
Yield: 15.0%.
<350° F. Yield: 10.4%.

EXAMPLE II

In this example the same starting propylene oligomers are used in the co-metathesis reaction with ethylene and under the same experimental conditions as in Example I. The co-metathesis conversion is 75% based on the propylene oligomers. In the $Cr/SiO_2$ catalyzed polymerization step, 72.5 grams of olefins and 4 grams of $Cr/SiO_2$ (3% Cr) are used. The polymerization is carried out at 110° C. for 116 hours. After hydrogenation over Pd/C at 50° C. and distillation in vacuum the following products are obtained:
650° F.+ lube:
Yield: 47.6%;
Viscosity at 100° C.; 35 cS;
VI: 159;
480°-650° F. diesel fuel:
Yield: 24.5%
NMR estimated cetane number: 71; no aromatics
Ignition behavior: T5=244.7° C.; T10=235.7° C.; T20=229.7° C.;
350°-480° F. kerosene/jet fuel:
Yield: 15.9%;
<350° F.:
Yield: 12.0%;

EXAMPLE III

Near-linear internal olefins are prepared by oligomerization of propylene in a continuous stirred tank reactor (CSTR) with <C12 olefins recycled to extinction at 210° C. and 0.3 WHSV. The conversion of propylene is 90%. The product oligomers which are near-linear internal olefins are subjected to co-metathesis with ethylene (80% conversion) followed by polymerization catalyzed by $Cr/SiO_2$ in the same manner as described in Example I. After hydrogenation and distillation, the following products are obtained: 650° F.+ lube:
Yield: 55.2%,
Viscosity at 100° C: 44.7 cS,
VI: 153;
480°-650° F. diesel fuel:
Yield: 25.4%;
350°-480° F. kerosene/jet fuel:
Yield: 13.8%
NMR estimated cetane number: 56; no aromatics
Ignition behavior: T5=251.4° C., T10=237.40° C.; T20=231.0° C.;
<350° F.:
Yield: 5.6%

A further embodiment of the instant invention comprises discovery that the <650° F.— fraction of near-linear paraffins recovered from the oligomerization of lower olefins using surface deactivated zeolite as catalyst, as taught in the cited references of Chen and Page, contain after hydrogenation diesel and kerosene boiling range aromatics-free fuels that exhibit high cetane values. Near-linear oligomers after hydrogenation yield slightly methyl branched paraffins which yield superior autoignition and low temperature performance properties desired in diesel fuels. In addition the high H/C ratio in these fuels lead to reduced particulate emissions when burned in diesel engines.

These embodiments of the present invention are illustrated in the following Example.

EXAMPLE IV

For comparison, two different batches of propylene oligomers are used. Both are prepared by using as the catalyst ZSM-23 surface deactivated 2,4,6-collidine. One batch (A) is prepared in a semi-continuous stirred tank reactor without recycle. The oligomerization is carried out at 200° C., 1000 psig with propylene fed on demand. The composition is shown in Table 1 and FIG. 1. The other batch (B) is prepared in twin fixed-bed reactors and with recycle of the $<C_{12}$ olefin oligomers (3:1 liquid) to extinction. The conditions are 230° C., 1000 psig, and WHSV of 0.2. The compositions are shown in Table II and FIG. 2.

The oligomers are fractionated under a reduced pressure using a ASTM D-2892 still to boiling point ranges close to number 1 fuel (B.P.: 350°-480° F.) and diesel fuel (B.P.:480°-650° F.). The fractions are hydrogenated at 150° C. using Ni on Kiselgel until no more hydrogen is taken up. The lack of olefin content of the final products is established by NMR. Cetane number, API gravity, freezing point are determined by the respective ASTM methods.

TABLE I

PROPYLENE OLIGOMERS PREPARED
SINGLE PASS IN A CSTR
(A)

| EXPERIMENTAL CONDITIONS | |
|---|---|
| Catalyst: | ZSM-23 treated with 2,4,6-collidine |
| Feed: | Propylene, fed on demand |
| Temperature: | 200° C. |
| Pressure: | 1000 psig |

| COMPOSITION | |
|---|---|
| Component | Wt. % |
| $C_6$ | 43.0 |
| $C_9$ | 25.2 |
| $C_{12}$ | 14.8 |
| $C_{15}$ | 9.6 |
| $C_{18}$ | 3.9 |
| $C_{21}$ and higher | 3.4 |

| BRANCHING | | |
|---|---|---|
| Component | Isomer | Wt. % |
| $C_9$ | Di-Me | 18.8 |
| | Mono-Me | 72.4 |
| | Normal | 8.9 |
| | $Me/C_9$ | 1.19 |
| $C_{12}$ | Di-Me | 22.9 |
| | Mono-Me | 69.4 |
| | Normal | 7.7 |
| | $Me/C_{12}$ | 1.27 |
| $C_{15}$ | Di-Me | 18.7 |
| | Mono-Me | 74.1 |
| | Normal | 7.3 |
| | $Me/C_{15}$ | 1.21 |

TABLE II

Propylene Oligomers Prepared in Twin Fixed-Bed Reactors
With $<C_{12}$ = Recycled To Extinction
(B)

| EXPERIMENTAL CONDITIONS | |
|---|---|
| Catalyst: | ZSM-23 treated with 2,4,6-collidine |
| Feed: | Propylene (60%) + Propane (40%) |
| WHSV: | 0.2 based on propylene |
| Temperature: | 230° C. |
| Pressure: | 1000 psig |
| Recycle: | 3:1 liquid, to extinction |

| COMPOSITION | |
|---|---|
| Component | Wt. % |
| $C_6$ | 2.7 |
| $C_9$ | 4.9 |

TABLE II-continued
Propylene Oligomers Prepared in Twin Fixed-Bed Reactors With <$C_{12}$ = Recycled To Extinction (B)

| | | |
|---|---|---|
| $C_{12}$ | | 47.5 |
| $C_{15}$ | | 26.4 |
| $C_{18}$ | | 11.0 |
| $C_{21}$ and higher | | 7.2 |

BRANCHING

| Component | Isomer | Wt. % |
|---|---|---|
| $C_{12}$ | Di-Me | 55.2 |
| | Mono-Me | 41.2 |
| | Normal | 3.6 |
| | Me/$C_{12}$ | 1.79 |
| $C_{15}$ | Di-Me | — |
| | Mono-Me | — |
| | Normal | — |
| | Ne/$C_{15}$ | 1.75 |

The yield and diesel properties from the two propylene oligomers after hydrogenation are summarized in Table III. It should be noted that propylene oligomers (olefins) are the only products from the oligomerization process and, as a result, the hydrogenated products have paraffinic structures only. Results of the GC/MS showed that greater than 96 wt % of the 350°–480° F. fraction is positively identified as $C_nH_{2n+2}$ paraffins by their molecular ions and fragmentation patterns; 3.0 wt % have no molecular ions; however, they show fragmentation which could be derived from $C_nH_{2n+2}$ paraffins. Only 0.4 wt %, by total ion integration, could belong to $C_nH_{2n}$ (olefins which were not completely hydrogenated or cycloalkanes, otherwise known as naphthenes). The 480°–650° F. fraction gave GC/MS results which showed all peaks are positively identified as $C_nH_{2n+2}$ paraffins by their molecular ions.

TABLE III
FUEL YIELD AND PROPERTIES FROM HYDROGENATED PROPYLENE OLIGOMERS

| Boiling Range, °F. | Yield % | Cetane Number | API Gravity | F.P. °C. | Mid BP °F. |
|---|---|---|---|---|---|
| (A) Oligomers-CSTR single pass, 1.3CH₃/12C: | | | | | |
| 350–600 | 31.7 | 60.6 | 52.7 | −54.4 | — |
| 350–480 | 14.5 | 59.4 | 54.1 | −62.5 | 424 |
| 480–650 | 17.2 | 73.7 | 48.4 | −19.3 | 539 |
| (B) Oligomers-2 fixed bed reactors, <$C_{12}$ = recycle, 1.8CH₃/12C | | | | | |
| 350–650 | 90.0 | 63.2 | 50.7 | −1.0 | 499 |
| 350–480 | 44.0 | 57.7 | 55.1 | −73.0 | 435 |
| 480–650 | 46.0 | 65.3 | 48.4 | −22.6 | 574 |

The foregoing Example illustrates the surprising discovery that particularly high cetane value fuels free of aromatics are recoverable following hydrogenation of the 650° F.− fraction of the oligomerization product of propene using surface deactivated catalyst. These oligomers have a unique near linear structure as shown by NMR. This unique structure, it is believed, is the distinguishing element responsible for providing such surprisingly high cetane values in a clean fuel free of aromatics.

While the invention has been described by reference to specific embodiments there is no intent to limit the scope of the invention except as described in the following claims.

What is claimed is:

1. A process for the co-production of lubricant range hydrocarbons and aromatics free hydrocarbon fuel having high cetane number, comprising:

a) contacting a feedstream comprising lower olefinic hydrocarbons with surface deactivated acidic, medium pore, shape selective metallosilicate catalyst particles under oligomerization conditions whereby a product stream comprising aromatics-free slightly branched internal olefin oligomers is produced;

b) contacting said aromatics-free slightly branched internal olefin oligomers and a fresh feedstream comprising excess ethylene with metathesis catalyst in a reaction zone under metathesis conditions whereby said internal olefin oligomers are converted to reaction product comprising slightly branched alpha-olefin oligmers and unconverted oligomers;

c) contacting step (b) metathesis reaction product with reduced valence state Group VIB metal catalyst on porous support under oligomerization conditions and recovering a reaction product containing a 350°–650° F. fuel boiling range portion and a 650° F.+ lubricant range portion;

d) separating and hydrogenating step (c) fuel boiling range portion whereby a hydrocarbon fuel having cetane number between 50 and 75 and no aromatics is produced.

2. The process of claim 1 wherein said lower olefinic hydrocarbons comprise $C_2$–$C_4$ 1-alkenes.

3. The process of claim 2 wherein said hydrocarbons comprise propene.

4. The process of claim 1 wherein said slightly branched internal olefin oligomer portion comprise hydrocarbons having about 1–2 methyl branches per 12 carbon atoms.

5. The process of claim 1 wherein said metathesis catalyst includes supported oxides of rhenium, molybdenum or tungsten.

6. The process of claim 5 further including tetraalkyl tin as co-catalyst.

7. The process of claim 5 wherein said catalyst comprises aluminum oxide supported rhenium oxide and tetra methyl tin.

8. The process of claim 1 wherein said metallosilicate catalyst includes surface deactivated ZSM-5 or ZSM-23.

9. The process of claim 1 wherein step (c) catalyst comprises CO reduced chromium oxide catalyst on silica support.

10. The process of claim 1 including the further steps of separating step (a) product stream to recover a $C_{11}$+ oligomer portion and reacting said $C_{11}$+ oligomer in step (b).

11. A process for the production of hydrocarbon fuels having high cetane value, comprising:

contacting a feedstream comprising lower olefinic hydrocarbons with surface deactivated acidic, medium pore, shape selective metallosilicate catalyst particles under oligomerization conditions whereby a product stream comprising aromatics-free near linear olefinic oligomers is produced, wherein said near linear oligomers contain less than 2.5 methyl groups per 12 carbon atoms;

hydrogenating at least a portion of said product stream and recovering a 350° F.–650° F. fuel boiling range fraction having a cetane value between 50 and 75, no aromatics and less than 0.5 weight percent naphthenes.

12. The process of claim 11 wherein said lower olefinic hydrocarbons comprise $C_2$–$C_4$ 1-alkenes.

13. The process of claim 12 wherein said hydrocarbons comprise propene.

14. The process of claim 11 wherein said metallosilicate catalyst includes surface deactivated ZSM-5 or ZSM-23.

15. The process of claim 11 wherein said near linear olefinic oligomers comprise hydrocarbons having about 1-2 methyl branches per 12 carbon atoms.

16. A hydrocarbon fuel composition having high cetane value comprising the reaction product of a process comprising the steps of:
  a) contacting a feedstream comprising lower olefinic hydrocarbons with surface deactivated acidic, medium pore, shape selective metallosilicate catalyst particles under oligomerization conditions whereby a product stream comprising aromatics-free slightly branched internal olefin oligomers is produced;
  b) contacting said aromatics-free slightly branched internal olefin oligomers and a fresh feedstream comprising excess ethylene with metathesis catalyst in a reaction zone under metathesis conditions whereby said internal olefin oligomers are converted to reaction product comprising slightly branched alpha-olefin oligomers and unconverted oligomer;
  c) contacting step (b) metathesis reaction product with reduced valence state Group VIB metal catalyst on porous support under oligomerization conditions and recovering a reaction product containing a 350° F.-650° F. fuel boiling range portion and a 650° F.+ lubricant range portion;
  d) separating and hydrogenating step (c) fuel foiling range portion containing no aromatics and less than 0.5 wt % napthenes whereby a clean hydrocarbon fuel having cetane number between 50 and 75 is produced.

17. The process of claim 16 wherein said lower olefinic hydrocarbons comprise propene.

18. The process of claim 16 wherein said slightly branched internal olefin oligomer portion comprise hydrocarbons having about 1-2 methyl branches per 12 carbon atoms.

19. The process of claim 16 including the further steps of separating step (a) product stream to recover a $C_{11}+$ oligomer portion and reacting said $C_{11}+$ oligomer in step (b).

20. A hydrocarbon fuel composition having high cetane number, comprising:
  an aromatics-free mixture of paraffinic hydrocarbons having a boiling range between 350° F. and 650° F., cetane number between 50 and 75 and containing less than 0.5 wt % naphthenes, said hydrocarbons containing about 1-2 methyl branches per 12 carbon atoms.

* * * * *